US012606532B2

(12) United States Patent
Vogt et al.

(10) Patent No.: US 12,606,532 B2
(45) Date of Patent: Apr. 21, 2026

(54) PREPARATION OF SUBSTITUTED 3-ARYL-5-TRIFLUOROMETHYL-1,2,4-OXADIAZOLES

(71) Applicant: BASF SE, Ludwigshafen (DE)

(72) Inventors: Florian Vogt, Ludwigshafen (DE); Kailaskumar Borate, Navi Mumbai (IN); Bernd Wolf, Ludwigshafen (DE); Christopher Koradin, Ludwigshafen (DE); Joachim Gebhardt, Ludwigshafen (DE); Roland Goetz, Ludwigshafen (DE); Harish Shinde, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 879 days.

(21) Appl. No.: 17/796,291

(22) PCT Filed: Feb. 1, 2021

(86) PCT No.: PCT/EP2021/052256
§ 371 (c)(1),
(2) Date: Jul. 29, 2022

(87) PCT Pub. No.: WO2021/156174
PCT Pub. Date: Aug. 12, 2021

(65) Prior Publication Data

US 2023/0145982 A1 May 11, 2023

(30) Foreign Application Priority Data

Feb. 5, 2020 (EP) .................................... 20155609
Feb. 20, 2020 (EP) .................................... 20158522
Nov. 3, 2020 (EP) .................................... 20205324

(51) Int. Cl.
*C07D 271/06* (2006.01)

(52) U.S. Cl.
CPC .................................. *C07D 271/06* (2013.01)

(58) Field of Classification Search
CPC .................................................... C07D 271/06
See application file for complete search history.

(56) References Cited

FOREIGN PATENT DOCUMENTS

WO WO-2015/185485 A1 12/2015
WO WO-2017/022295 A1 2/2017
WO WO-2017/211649 A1 12/2017
WO WO-2017/222951 A1 12/2017
WO WO-2017/222952 A1 12/2017
WO WO-2019/020451 A1 1/2019
WO WO-2019/020501 A1 1/2019

OTHER PUBLICATIONS

Durden, et al., "Reaction of "activated" esters with amidoximes. Convenient synthesis of 1,2,4-oxadiazoles", The Journal of Organic Chemistry, vol. 36, Issue 9, May 1, 1971, pp. 1306-1307.
European Search Report for EP Patent Application No. 20155609.9, Issued on Jul. 22, 2020, 4 pages.
Hemming, "Product Class 6: 1,2,4-Oxadiazoles", Science of Synthesis, Category 2: Hetarenes and Related Ring Systems, vol. 13: Five-Membered Hetarenes with Three or More Heteroatoms, ed. Storr, et al., 2004, pp. 127-184.
International Patent Application No. PCT/EP2021/052256, International Search Report and Written Opinion, Issued on Feb. 23, 2021.
Tale, et al., "Synthesis and anti-bacterial, anti-fungal activity of novel 1,2,4-oxadiazole", Journal of Chemical and Pharmaceutical Research, vol. 3, Issue 2, 2011, pp. 496-505.

*Primary Examiner* — Shawquia Jackson
(74) *Attorney, Agent, or Firm* — MARSHALL, GERSTEIN & BORUN LLP

(57) ABSTRACT

The present invention relates to a process for the preparation of substituted 3-aryl-5-trifluoromethyl-1,2,4-oxadiazoles of formula I, which can be obtained through reaction of amidoxime compounds of formula II with a haloacetic ester in the presence of a solvent and a base.

(I)

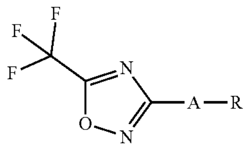

(II)

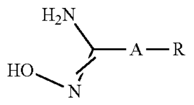

19 Claims, No Drawings

PREPARATION OF SUBSTITUTED 3-ARYL-5-TRIFLUOROMETHYL-1,2,4-OXADIAZOLES

CROSS-REFERENCE TO RELATED APPLICATIONS

This is the U.S. national phase of International Application No. PCT/EP2021/052256, filed Feb. 1, 2021, which claims the benefit of European Patent Application No. 20155609.9, filed on Feb. 5, 2020, European Patent Application No. 20158522.1, filed Feb. 20, 2020, and European Patent Application No. 20205324.5, filed Nov. 3, 2020.

The present invention relates to a process for the preparation of substituted 3-aryl-5-trifluoromethyl-1,2,4-oxadiazoles of formula I, which can be obtained through reaction of amidoxime compounds of formula II with a haloacetic ester in the presence of a solvent and a base.

I

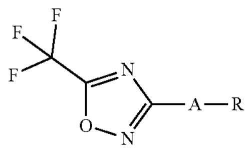

II

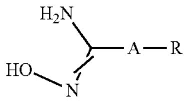

Substituted 3-aryl-5-trifluoromethyl-1,2,4-oxadiazoles are known to be useful for controlling phytopathogenic fungi, for example from WO 2015/185485 A1 and WO 2017/211649 A1.

Typically, the preparation of 3-aryl-5-trifluoromethyl-1,2,4-oxadiazoles involves the formation of the oxadiazole ring through the reaction of amidoxime compounds, for example compounds of formula II, with an activated derivative of trifluoroacetic acid (TFA). In the first reaction step the hydroxy group in compounds of formula II is acylated. Subsequently, the intermediate O-trifluoroacetyl amidoximes undergo ring closure with concomitant elimination of water to form the oxadiazole moiety.

Trifluoroacetic acid anhydride (TFAA) is commonly used as an acylating agent. In the above reaction at least two equivalents of acylating agent are necessary to ascertain the complete conversion of compounds II. Hence, if TFAA is used, a total amount of at least three equivalents TFA is formed per equivalent of compounds II, which must be discarded. TFAA is rather expensive and for the sake of atom efficiency there is an interest to reduce the excess amounts of TFA furnished during or after the ring closing reaction.

WO 2019/020451 A1 discloses the use of trifluoroacetic halides instead of TFAA, which results in the formation of a comparatively smaller amount of TFA. The reaction, however, still furnishes significant amounts of TFA along with hydrogen halides, which may cause corrosion of reaction equipment and eventually the hydrogen halides must be separated from the reaction product. Trifluoroacetic halides boil at low temperatures and are thus not easy to handle and, since they are also highly toxic, pose risks for the operator, particularly in large scale setups.

The transformations described in the references above generate considerable amounts of TFA that must be separated from the reaction product and discarded. To increase atom efficiency, trifluoroacetic acid esters (TFAE) may be used in these processes, which are less reactive towards amidoximes of formula II than TFAA or trifluoroacetic halides. In theory, the use of esters instead of the corresponding acid halides or anhydrides requires, if any, only a small excess of the acylating agent.

Durden et al. in *Journal of Organic Chemistry* 1971, 36, 9, 1306-1307, describe a process, in which (halo)acetic acid vinylesters are used in reactions with benzamidoxime to obtain the corresponding oxadiazoles. The reported yields with trifluoroacetic acid vinylesters are moderate (43%).

WO 2017/22295 A1, WO 2017/222951 A1, and WO 2017/222952 A1 disclose the preparation of 3-aryl-5-trifluoromethyl-1,2,4-oxadiazoles using methyl trifluoroacetate in the presence of potassium carbonate as the base, in a mixture of DMF and toluene as the solvent, and at a temperature of 80° C. The reported yields are also moderate.

In view of the above, it was an object of the present invention to overcome these disadvantages and to provide an improved and more economical and production plant friendly process, which enables the preparation of 3-aryl-5-trifluoromethyl-1,2,4-oxadiazoles on an industrial scale in high yield and with low amounts of side-products.

The inventors found that alkyl esters of trifluoroacetic acid may be reacted with amidoxime compounds of formula II in the presence of metal alkoxylates, which surprisingly provides higher yields of the desired oxadiazoles than the procedures of the prior art.

The process of this invention is eco-friendly and more cost efficient than previously reported processes as it employs readily available, non-toxic and cheap reactants. The reaction may be performed with comparatively low excess of the acylating agent having regard to the amidoxime starting material. Furthermore, fast conversion of the starting material is achieved at comparatively lower reaction temperatures.

Accordingly, the present invention relates to a process for preparing compounds of formula I,

I

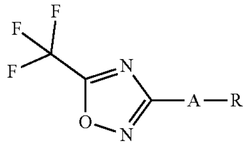

wherein

A is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein A is further unsubstituted or further substituted with additional n identical or different radicals $R^A$; wherein n is 0,1, 2, 3, or 4;

$R^A$ is independently selected from the group consisting of halogen, cyano, $C_1$-$C_6$-alkyl, $C_1$-$C_6$-haloalkyl, $C_1$-$C_6$-alkoxy, and $C_1$-$C_6$-haloalkoxy;

R is methyl, chloromethyl, hydroxymethyl, trichloromethyl, ethyl, iso-propyl, OH, SH, cyano, halogen, $CH_2F$, $CHF_2$, 2,2,2-trifluoroethyl, cyclopropyl, $—C(=O)H$, $—C(=NOR^2)H$, $—C(=O)OH$, $—C(=O)OR^1$, $—C(=W)NR^1R^2$, $—CR^3R^4NR^1R^2$, —$CR^3R^4OR^1$, —$CR^3$(=$NR^1$), —$CR^3$(=O), —$CR^3R^4C$(=O)OH, —$CR^3R^4C$(=O)$R^1$, —$CR^3R^4C$(=W)$NR^1R^2$, —$OCR^3R^4C$(=O)OH, —$OCR^3R^4C$(=O)$R^1$, —$OCR^3R^4C$(=W)$NR^1R^2$, —$CR^3R^4$—N($R^2$)—C(=W)$R^1$, —$CR^3R^4S$(=O)$_2R^1$, or —$CR^3R^4$—N($R^2$)—S(=O)$_2R^1$; wherein W is O or S;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(=O)—$C_1$-$C_6$-alkyl, —C(=O)—$C_3$-$C_{11}$-cycloalkyl, or —C(=O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

$R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(=O)—$C_1$-$C_6$-alkyl, —C(=O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_3$-cycloalkyl, —$NHSO_2$—$C_1$-$C_4$-alkyl, —C(=O)—$C_1$-$C_4$-alkyl, —C(=O)—O—$C_1$-$C_4$-alkyl, $C_1$-$C_6$-alkylsulfonyl, hydroxy$C_1$-$C_4$-alkyl, —C(=O)—$NH_2$, —C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^3$, $R^4$ independently of each other are selected from the group consisting of hydrogen, halogen, cyano, $C_1$-$C_4$-alkyl, $C_1$-$C_4$-alkenyl, $C_1$-$C_4$-alkynyl, $C_1$-$C_4$-haloalkyl and $C_1$-$C_4$-alkoxy; or $R^3$ and $R^4$ together with the carbon atom to which they are bound form a cyclopropyl group;

the process comprising reacting an amidoxime of formula II,

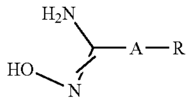

II wherein the variables A and R are as defined above for compounds of formula I, with a haloacetic ester of formula II.a,

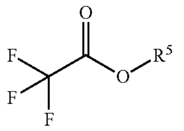

II.a wherein $R^5$ is $C_1$-$C_6$-alkyl, in the presence of a solvent and a base; whereas the process is characterized in that the base comprises a metal alkoxylate of formula IV, $$[C_1\text{-}C_6\text{-alkyl-O}]_xM^{x+} \qquad \text{IV}$$

wherein the metal M is an alkali metal, wherein x is 1, or M is a divalent alkaline earth metal, wherein x is 2; and the solvent comprises an alkyl alcohol of formula III, or mixtures thereof, $$C_1\text{-}C_6\text{-alkyl-OH} \qquad \text{III.}$$

In one aspect of the present invention the variable A is phenyl in compounds of formula I and II.

In one embodiment of the present invention radical $R^A$ in compounds of formula I and II is halogen, $C_1$-$C_6$-alkyl, $C_1$-$C_6$-haloalkyl, $C_1$-$C_6$-alkoxy, or $C_1$-$C_6$-haloalkoxy; particularly fluorine.

In one aspect n is 1 and $R^A$ is fluorine in compounds of formula I and II.

In a preferred embodiment the variable n is 0 in compounds of formula I and II.

In one aspect the present invention relates to a process as defined above, wherein the amidoxime is of formula II.b,

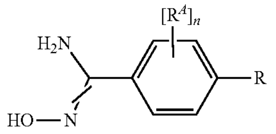

II.b wherein n is 0 or 1; and wherein the meaning of R is as defined or preferably defined herein for compounds of formula I; and wherein $R^A$ is selected from the group consisting of halogen, $C_1$-$C_6$-alkyl, $C_1$-$C_6$-haloalkyl, $C_1$-$C_6$-alkoxy, and $C_1$-$C_6$-haloalkoxy; to obtain oxadiazoles of formula I.b, I.b

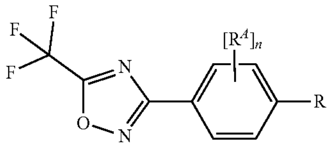

wherein the variables n, $R^A$, and R have the meaning as defined for compounds II.b.

In another embodiment n is 1 and $R^A$ is fluorine in compounds of formula I.b and II.b.

In a preferred embodiment n is 0 in compounds of formula I.b and II.b.

In one embodiment the variables in compounds of formula I, II, I.b, and II.b have the following meaning:

$R^A$ is fluorine;

n is 0 or 1;

R is methyl, chloromethyl, hydroxymethyl, trichloromethyl, —C(═O)H, —C(═NOR$^2$)H, —C(═O)OH, OH, SH, cyano, halogen, —C(═O)NR$^1$R$^2$, —CH$_2$—N(R$^2$)—C(═O)R$^1$, —CH$_2$—N(R$^2$)—S(═O)$_2$R$^1$,

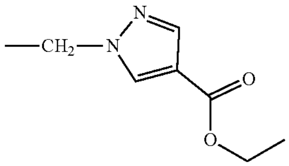

or

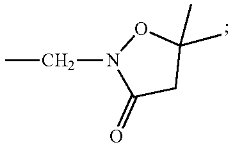

;

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl;

$R^2$ is hydrogen, methyl, ethyl, methoxy, ethoxy, or cyclopropyl.

In a further embodiment the variables in compounds of formula I, II, I.b, and II.b have the following meaning:

$R^A$ is fluorine;

n is 0 or 1;

R is methyl, —C(═O)OH, —C(═O)NR$^1$R$^2$, —CH$_2$—N(R$^2$)—C(═O)R$^1$, —CH$_2$—N(R$^2$)—S(═O)$_2$R$^1$,

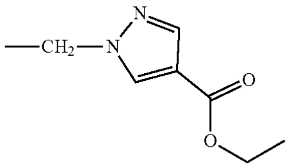

or

-continued

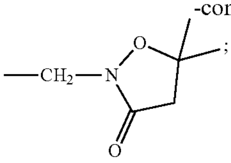

;

$R^1$ is $C_1$-$C_6$-alkly, phenyl, or cyclopropyl, wherein the phenyl ring is unsubstituted or substituted with 1, 2, 3, or 4 identical or different groups selected from halogen;

$R^2$ is hydrogen, methyl, ethyl, methoxy, ethoxy, or cyclopropyl.

In yet another embodiment the variables in compounds of formula I, II, I.b, and II.b have the following meaning:

$R^A$ is fluorine;

n is 0 or 1;

R is —CH$_2$—N(R$^2$)—C(═O)R$^1$, —CH$_2$—N(R$^2$)—S(═O)$_2$R$^1$,

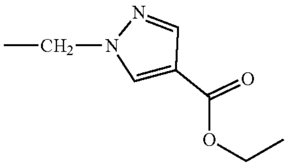

or

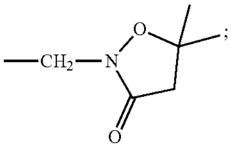

;

$R^1$ is $C_1$-$C_6$-alkly, or cyclopropyl;

$R^2$ is hydrogen, methyl, methoxy, ethoxy, or cyclopropyl.

In another embodiment the variables in compounds of formula I, II, I.b, and II.b have the following meaning:

$R^A$ is fluorine;

n is 0 or 1;

R is methyl, —C(═O)OH, or —C(═O)NR$^1$R$^2$;

$R^1$ is methyl or phenyl, wherein the phenyl ring is unsubstituted or substituted with 1, 2, 3, or 4 identical or different groups selected from halogen;

$R^2$ is hydrogen, methyl, ethyl, methoxy, or ethoxy.

In still another embodiment the variables in compounds of formula I, II, I.b, and II.b have the following meaning:

n is 0;

R is —C(═O)NR$^1$R$^2$;

$R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl;

$R^2$ is hydrogen.

In one embodiment of the invention radical $R^5$ in haloacetic esters of formula II.a is methyl, ethyl, n-propyl, iso-propyl, or n-butyl; preferably methyl or ethyl; particularly ethyl.

In one embodiment the reaction is conducted using 1 to 5 molar equivalents of the haloacetic ester II.a, based on the amount of the amidoxime II. Preferably, 1 to 3 molar equivalents are used, particularly 1.5 to 2.5 molar equivalents, or 1.2 to 2 molar equivalents are used, even more preferred 1.5 to 2.2 molar equivalents, or 1.2 to 1.6 molar equivalents are used, based on the amount of the amidoxime II.

Typically, the haloacetic ester of formula II.a is added to a solution of amidoxime II and the base in the solvent. In one embodiment the total amount of haloacetic ester II.a is added to the reaction mixture in portions or continuously within 2-8 hours.

In another embodiment the base, or a solution of the base in the solvent, is added to a mixture of the amidoxime II and the haloacetic ester II.a, both optionally dissolved or partly dissolved in the solvent. In one embodiment the total amount of the base is added to the reaction mixture in portions or in a continuous way within 2-8 hours.

In a preferred embodiment the metal M in metal alkoxylates of formula IV is sodium, potassium, or magnesium; more preferably sodium or potassium; particularly sodium.

In a more preferred embodiment the metal alkoxylates IV is sodium methoxide or sodium ethoxide, or a mixture thereof.

In one embodiment of the present invention the alkoxylate base of formula IV is the corresponding conjugate Bronsted base of the solvent of formula III.

In a particularly preferred embodiment the metal alkoxylate IV is sodium methoxide and the solvent is methanol.

In another particularly preferred embodiment the metal alkoxylate IV is sodium ethoxide and the solvent is ethanol.

Typically, the base is added to the reaction mixture as a solution in the alkyl alcohol of formula III, which is the corresponding conjugated Bronsted acid of the base.

The base is used in an amount of at least 80 mol % based on the amount of the compound of formula II, or at least 100 mol %, or at least 150 mol %. In another aspect of the present invention the base is used in an amount that ranges between 80 and 1000 mol %, preferably between 80 and 500 mol %, more preferably between 90 and 200 mol %, particularly between 90 and 140 mol %, based on the amount of the compound of formula II.

The process may be carried out in the presence of an inert solvent, herein also referred to as auxiliary solvent. Suitable auxiliary solvents are, for example, aliphatic, cycloaliphatic and aromatic hydrocarbons (pentane, hexane, petroleum ether, cyclohexane, methylcyclohexane, benzene, toluene, xylene), aliphatic halogen-hydrocarbons(methylene chloride, chloroform, di- and tetrachloroethane), nitriles (acetonitrile, propionitrile, benzonitrile), ethers (diethylether, dibutylether, tert-butylmethylether, ethylene glycol dimethyl ether, ethylene glycol, diethyl ether, diethylene glycol dimethyl ether, 2-methyltetrahydrofuran, tetrahydrofuran, dioxane, diethylene, glycol monomethyl- or monoethyl ether), N-substituted lactams (N-methylpyrrolidone), carboxamides (N,N-dimethylformamide, N,N-dimethylacetamide), acyclic ureas (dimethyl imidazolinum), nitriles as acetonitrile or propionitrile, and sulphoxides and sulphones (dimethyl sulfoxide, dimethyl sulfone, tetramethylene sulfoxide, tetramethylene sulfone).

Preferred auxiliary solvents are benzene, toluene, xylene, cyclohexane, n-hexane, n-heptane, tetrahydrofuran, dioxane, N,N-dimethylformamide, N-methylpyrrolidine, or dimethyl sulfoxide.

According to the invention the solvent comprises an alkyl alcohol of formula III, or mixtures thereof, $C_1$-$C_6$-alkyl-OH III.

Specifically, in one embodiment of the present invention, the process is conducted in the presence of a solvent comprising methanol, ethanol, n-propanol, iso-propanol, n-butanol, iso-butanol, sec-butanol, or tert-butanol, or mixtures thereof.

In a particularly preferred embodiment the process is conducted in the presence of a solvent comprising methanol or ethanol, or mixtures thereof.

In one aspect the process is conducted in the presence of a solvent comprising an alkyl alcohol of formula III as defined or preferably defined above, whereas the solvent contains at least 1% by volume of the alkyl alcohol of formula III, or mixtures thereof, based on the total amount of solvents, i.e. besides any further solvents; whereas such further solvents include auxiliary solvents or the haloacetic ester of formula II.a, or mixtures thereof.

In another aspect the process is conducted in the presence of a solvent comprising an alkyl alcohol of formula III as defined or preferably defined above, whereas the solvent contains at least 5% by volume of the alkyl alcohol of formula III, or mixtures thereof, based on the total amount of solvents, i.e. besides any further solvents; whereas such further solvents include auxiliary solvents or the haloacetic ester of formula II.a, or mixtures thereof.

In one aspect the process is conducted in the presence of an alkyl alcohol of formula III, or mixtures thereof, and in the absence of any further auxiliary solvents.

The reaction temperature of the above process is preferably in the range of from 0° C. to 60° C.; preferably in the range of from 10° C. to 50° C. or in the range of from 20° C. to 50° C.

The reaction is generally carried out within 10 minutes to 20 hours, or within 60 minutes to 14 hours, preferably within 1 to 10 hours, or within 2 to 10 hours, more preferably within 2 to 8 hours.

In a particularly preferred embodiment the process is conducted in the presence of a solvent comprising methanol or ethanol, or mixtures thereof; and wherein the metal alkoxylates IV is sodium methoxide or sodium ethoxide, or a mixture thereof; and wherein the reaction temperature of the above process is in the range of from 0° C. to 60° C.

In another particularly preferred embodiment the process is conducted in the presence of a solvent comprising an alkyl alcohol comprising methanol, ethanol, n-propanol, iso-propanol, n-butanol, iso-butanol, sec-butanol, or tert-butanol, or mixtures thereof; and wherein the alkoxylate base of formula IV corresponds to the conjugate Bronsted base of said alkyl alcohol; and wherein the reaction temperature of the above process is in the range of from 0° C. to 60° C.; and whereas the solvent contains at least 1% by volume of the alkyl alcohol, or mixtures thereof, based on the total amount of solvents, i.e. besides any further solvents; whereas such further solvents include auxiliary solvents or the haloacetic ester of formula II.a, or mixtures thereof.

In still another particularly preferred embodiment the process is conducted in the presence of a solvent comprising methanol or ethanol, or mixtures thereof; and wherein the metal alkoxylates IV is sodium methoxide or sodium ethoxide, or a mixture thereof; and wherein the reaction temperature of the above process is in the range of from 0° C. to 60° C.; and whereas the solvent contains at least 1% by volume of the alkyl alcohol of formula III, or mixtures thereof, based on the total amount of solvents, i.e. besides any further solvents; whereas such further solvents include auxiliary solvents or the haloacetic ester of formula II.a, or mixtures thereof; or even more preferably if the alkoxylate base of formula IV corresponds to the conjugate Bronsted base of the solvent of formula III.

In yet another particularly preferred embodiment the process is conducted in the presence of a solvent comprising methanol or ethanol, or mixtures thereof; and wherein the metal alkoxylates IV is sodium methoxide or sodium ethoxide, or a mixture thereof; and wherein the reaction temperature of the above process is in the range of from 10° C. to 50° C.; and whereas the solvent contains at least 5% by volume of the alkyl alcohol of formula III, or mixtures thereof, based on the total amount of solvents, i.e. besides any further solvents; whereas such further solvents include auxiliary solvents or the haloacetic ester of formula II.a, or mixtures thereof; or even more preferably if the alkoxylate base of formula IV corresponds to the conjugate Bronsted base of the solvent of formula III.

The process of the present invention is typically carried out at atmospheric pressure. In another embodiment the process is conducted in a closed reactor for avoiding losses of low boiling compound III by vapor pressure or nitrogen purge. A little overpressure is generated in this case by heating or dosage of one of the starting materials.

In a preferred embodiment (embodiment E.1) of the present invention the metal M in metal alkoxylates IV is sodium, potassium or magnesium.

Embodiment E.2: is based on embodiment E.1, wherein the radical $R^5$ in haloacetic esters of formula II.a is methyl or ethyl.

Embodiment E.3: is based on embodiment E.2, wherein the amount of the haloacetic ester of formula II.a is between 1.5 to 2.5 equivalents based on the amount of amidoxime II.

Embodiment E.4: is based on embodiment E.3, wherein the metal alkoxylates IV is sodium methoxide or sodium ethoxide, or a mixture thereof.

Embodiment E.5: is based on embodiment E.4, wherein the solvent comprises an alkyl alcohol of formula III, or mixtures thereof.

Embodiment E.6: is based on embodiment E.5, wherein the solvent comprises methanol or ethanol, or mixtures thereof.

Embodiment E.7: is based on embodiment E.6, wherein the alkoxylate base of formula IV corresponds to the conjugate Bronsted base of the solvent of formula III.

Embodiment E.8: is based on embodiment E.7, wherein the process is conducted in the presence of a solvent comprising an alkyl alcohol of formula III as defined or preferably defined herein, whereas the solvent contains at least 1% by volume of the alkyl alcohol of formula III, or mixtures thereof, based on the total amount of solvents, i.e. besides any further solvents; whereas such further solvents include auxiliary solvents or the haloacetic ester of formula II.a, or mixtures thereof.

Embodiment E.9: is based on embodiment E.8, wherein the process is conducted at a temperature in the range of from 0° C. to 60° C.

Embodiment E.10: is based on embodiment E.4, wherein the process is conducted at a temperature in the range of from 0° C. to 60° C.

Embodiment E.11: is based on embodiment E.9, wherein the variables in compounds of formula I, II, I.b, and II.b have the following meaning:

$R^A$ is fluorine;

n is 0 or 1;

R is methyl, chloromethyl, hydroxymethyl, trichloromethyl, —C(=O)H, —C(=NOR$^2$)H, —C(=O)OH, OH, SH, cyano, halogen, —C(=O)NR$^1$R$^2$, —$CH_2$—N(R$^2$)—C(=O)R$^1$, —$CH_2$—N(R$^2$)—S(=O)$_2$R$^1$,

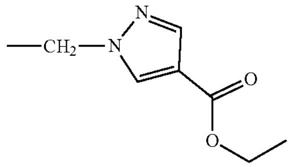

or

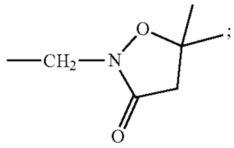

;

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl;

$R^2$ is hydrogen, methyl, ethyl, methoxy, ethoxy, or cyclopropyl.

Embodiment E.12: is based on embodiment E.9, wherein the variables in compounds of formula I, II, I.b, and II.b have the following meaning:

$R^A$ is fluorine;

n is 0 or 1;

R is methyl, —C(=O)OH, or —C(=O)NR$^1$R$^2$;

$R^1$ is methyl or phenyl, wherein the phenyl ring is unsubstituted or substituted with 1, 2, 3, or 4 identical or different groups selected from halogen;

$R^2$ is hydrogen, methyl, ethyl, methoxy, or ethoxy.

Embodiment E.13: is based on embodiment E.10, wherein the variables in compounds of formula I, II, I.b, and II.b have the following meaning:

$R^A$ is fluorine;

n is 0 or 1;

R is methyl, chloromethyl, hydroxymethyl, trichloromethyl, —C(=O)H, —C(=NOR$^2$)H, —C(=O)OH, OH, SH, cyano, halogen, —C(=O)NR$^1$R$^2$, —$CH_2$—N(R$^2$)—C(=O)R$^1$, —$CH_2$—N(R$^2$)—S(=O)$_2$R$^1$,

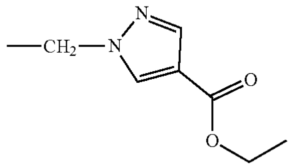

or

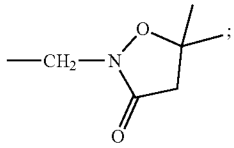

;

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl;

$R^2$ is hydrogen, methyl, ethyl, cyclopropyl, methoxy, or ethoxy.

Embodiment E.14: is based on embodiment E.10, wherein the variables in compounds of formula I, II, I.b, and II.b have the following meaning:

$R^A$ is fluorine;

n is 0 or 1;

R is methyl, —C(═O)OH, or —C(═O)$NR^1R^2$;

$R^1$ is methyl or phenyl, wherein the phenyl ring is unsubstituted or substituted with 1, 2, 3, or 4 identical or different groups selected from halogen;

$R^2$ is hydrogen, methyl, ethyl, methoxy, or ethoxy.

In a further embodiment of the invention a compound of formula I or I.b, wherein R is methyl, is converted into valuable chemical products or intermediates.

Accordingly, in one embodiment, compounds of formula I.b, wherein, n is 0 and R is methyl, can be further chlorinated to obtain a compound of formula I.c

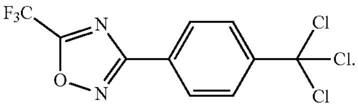

I.c

The chlorination of the methyl group R of compounds of formula I or I.b can be achieved as described in WO 2019/020451 A1 and the references cited therein.

In a further embodiment the compound of formula I.c is hydrolyzed to obtain a compound of formula III.a

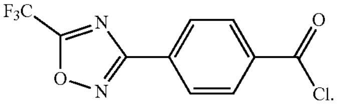

III.a

In one embodiment this transformation is carried out in the presence of catalytic amounts of a Lewis acid and water to obtain a compound of formula III.a, as described in WO 2019/020451 A1 and the references cited therein. Preferably, the Lewis acid is a metal salt, for example aluminum(III) chloride or iron(III) chloride, particularly iron(III) chloride.

In another embodiment the compound of formula I.b, wherein n is 0 and R is —C(═O)OH, is chlorinated to obtain a compound of formula III.a,

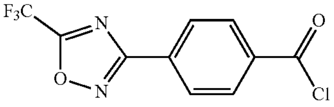

III.a

These transformations are described in WO 2019/020451 A1 and WO 2017/211649 A1 and the references cited therein.

In one embodiment, the compound of formula III.a is reacted with an amine of formula IV, $R^1$—NH—$R^2$ IV wherein $R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_3$-cycloalkyl, —$NHSO_2$—$C_1$-$C_4$-alkyl, (C═O)—$C_1$-$C_6$-alkyl, C(═O)—O—$C_1$-$C_6$-alkyl, $C_1$-$C_6$-alkylsulfonyl, hydroxy$C_1$-$C_4$-alkyl, C(═O)—$NH_2$, C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

to obtain a compound of formula V

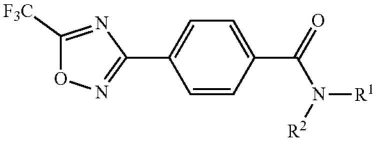

V

These transformations are also described in WO 2019/020451 A1 and WO 2017/211652 A1 and the references cited therein.

In another embodiment, the compound of formula V is used to obtain a compound of formula VI,

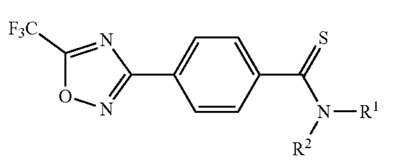

VI as described in WO 2019/020451 A1 and WO 2017/211649 A1 and the references cited therein.

In a preferred embodiment the variables $R^1$ and $R^2$ in compounds of formula I, I.b, II.b, IV, V and VI have the following meaning:

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, OH, $NH_2$, methyl, ethyl, methoxy, trifluoromethyl, trifluoromethoxy, difluoromethyl, difluoromethoxy, and cyclopropyl; and $R^2$ is hydrogen, methyl, or ethyl.

In another preferred embodiment the variables $R^1$ and $R^2$ in compounds of formula I, I.b, II.b, IV, V and VI have the following meaning:

$R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl; and $R^2$ is hydrogen.

The amidoxime compounds of formula II or II.b can be prepared from cyano compounds of formula V,

N≡C-A-R    V wherein the variables A and R are as defined or preferably defined herein for compounds of formula I or I.b, by treatment with hydroxylamine or its hydrochloride salt, in the presence of a base, preferably triethylamine, sodium hydroxide or sodium methylate, in a suitable solvent, such as methanol, ethanol or water, or a mixture of these solvents, at a temperature between 0° C. and 100° C. For related examples see Kitamura, S. et al *Chem. Pharm. Bull.* 2001, 49, 268 or any one of the patent references cited above. Compounds of formula V are either commercially available or may be prepared using standard procedures known to a person skilled in the art from readily available starting materials.

In a particularly advantageous two-step approach (reaction scheme below) a cyano compound of formula V.a, wherein the variables $R^1$ and $R^2$ are as defined or preferably defined herein, is reacted with hydroxylamine, or its hydrochloride salt, or its hydrogen sulfate salt in an alcohol solvent of formula III as defined or preferably defined herein, and optionally in the presence of a base, to obtain compounds of formula II.b, which can then be reacted with a trifluoroacetic ester of formula II.a in the presence of a base IV in accordance with the process of the present invention to prepare compounds of formula I.b.

This two-step sequence can be conducted using the same solvent of formula V in both consecutive steps and without the need for changing the reaction vessel between steps, therefore not requiring the isolation and handling of compound II.b. This two-step transformation is particularly preferred in regard to compounds V.a, II.b and I.b, wherein $R^1$ is hydrogen and $R^2$ is 2-fluorophenyl; and wherein the solvent III is methanol, ethanol, iso-propanol, n-butanol, or 2-butanol; particularly methanol or ethanol; and wherein the base IV in the second step is sodium ethanolate or sodium methanolate.

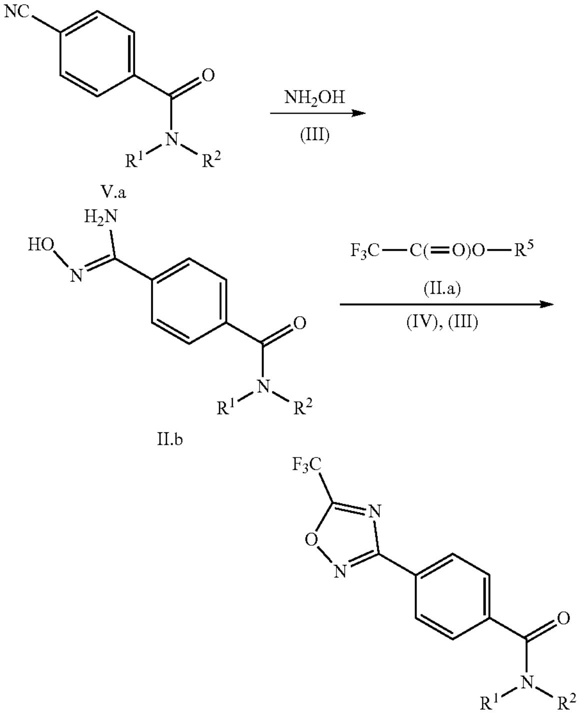

V.a

II.b

I.b

The term "auxiliary solvent" herein refers to an inert solvent, i.e. a solvent, which is not taking part in the reaction and is not an alkyl alcohol that falls under the definition of compounds of formula III. This means that the auxiliary solvent is not identical with the reactants (the amidoxime II and the haloacetic ester of formula II.a).

The term "conjugate Bronsted base" refers to the commonly definition, whereas it is a member of a pair of compounds that transform into each other by gaining or losing a proton, whereas the conjugate base is the species which has given off the proton.

In the definitions of the variables given above, collective terms are used which are generally representative for the substituents in question.

The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl(allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2, 2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH-group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $(C_1$-$C_4$-alkyl$)_2$N-group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl(bicyclo[4.1.0]heptyl) and norbornyl(bicyclo[2.2.1]heptyl).

The terms "—C(═O)—$C_1$-$C_6$-alkyl", "—C(═O)—O—$C_1$-$C_6$-alkyl" and "—C(═O)—$C_3$-$C_{11}$-cycloalkyl" refer to aliphatic radicals which are attached through the carbon atom of the —C(═O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_8$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydro-furanyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,2-,-3-,-4-,-5,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-, -6- or -7-yl, hexahydroazepin-1-,-2-,-3- or 4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Analytical method 1: HPLC Agilent 1100 Series; column: Agilent Zorbax Phenyl-Hexyl 1.8 μm 50*4.6 mm, Column Flow: 1 mL/min, time: 25 min, pressure: 20000 kPa; temperature: 20° C.; wavelength 200 nm; injector volume: 2 uL; retention time of the respective products is based on reference material.

Eluent: A: Water with 0.1 Vol % $H_3PO_4$; B: Acetonitrile

| Time (min) | % B | Rate (mL/min) |
|---|---|---|
| 0.0 | 14 | 1.0 |
| 16.0 | 86 | 1.0 |
| 20.0 | 86 | 1.0 |
| 20.1 | 14 | 1.0 |

Analytical method 2: HPLC Agilent 1100 Series; column: Agilent Zorbax Eclipse XDB-C18 1.8 μm 50*4.6 mm von Agilent, Column Flow: 1.3 mL/min, time: 10 min, pressure: 23000 kPa; temperature: 20° C.; wavelength 195 nm; injector volume: 1 uL; retention time of the respective products is based on reference material and given below.

Eluent: A: Water with 0.1 Vol % $H_3PO_4$; B: Acetonitrile

| Time (min) | % B | Rate (mL/min) |
|---|---|---|
| 0.0 | 0 | 1.3 |
| 2.0 | 0 | 1.3 |
| 5.0 | 80 | 1.3 |
| 6.0 | 100 | 1.3 |
| 8.0 | 100 | 1.3 |
| 8.1 | 0 | 1.3 |

Example 1) Preparation of 3-(p-tolyl)-5-(trifluoromethyl)-1,2,4-oxadiazole

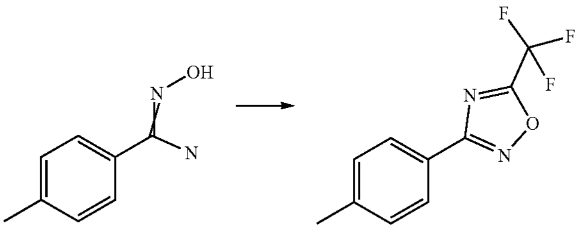 [SMILES: Cc1ccc(C(N)=NO)cc1 ; Cc1ccc(-c2noc(C(F)(F)F)n2)cc1]

A vessel was charged at 22° C. with 40.0 g (256 mmol, purity 96.0%) of N'-hydroxy-4-methyl-benzamidine and 181 g (1.28 mol) of ethyl trifluoroacetate. 27.6 g sodium methanolate (151 mmol, 30% w/w in methanol) was added within 30 minutes and the reaction mixture was stirred for 1.5 hours at 30° C. Then, another portion of 13.8 g sodium methanolate (75.5 mmol, 30% w/w in methanol) was added within 10 minutes and the mixture was stirred for additional 40 minutes. A final portion of 13.8 g sodium methanolate (75.5 mmol, 30% w/w in methanol) was added within 10 minutes and the mixture was stirred for additional 30 minutes. 2.3 g hydrochloric acid (32% w/w) was added and all volatiles were removed under reduced pressure. Water (60 g) was added and the phases were separated. 57.4 g (94.8%, HPLC purity (method 1): 96.3%) of the title compound was isolated from the organic phase.

Example 2) Preparation of N-(2-fluorophenyl)-4-[5-(trifluoromethyl)-1,2,4-oxadiazol-3-yl]benzamide

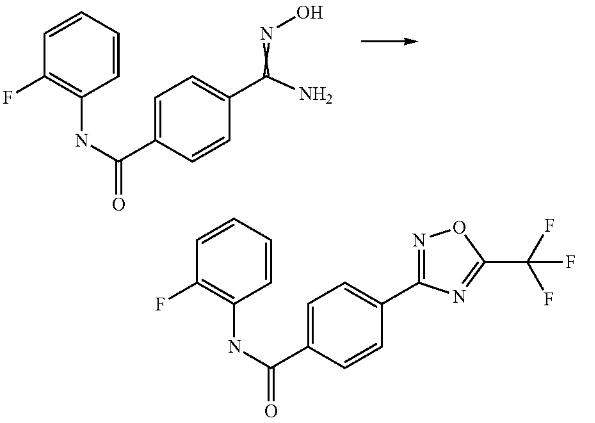

Example 2.1) TFAE as Reagent

A flask was charged with 500 mg (1.83 mmol) of N-(2-fluorophenyl)-4-[(Z)—N'-hydroxycarbamimidoyl]benzamide and 5 mL of N,N-dimethylformamide at room temperature. To this reaction mass 416 mg (2.93 mmol) of ethyl trifluoroacetate was added at room temperature followed by dropwise addition of 527 mg sodium methanolate (2.93 mmol, 30% w/w in methanol). Slight exotherm was observed during this addition and the reaction mass turned reddish brown. The reaction mass was stirred at room temperature for 1 further hour. HPLC analysis confirmed complete conversion. Then, water was added to the reaction mass, which caused the product to precipitate. The product was filtered and the filter cake was washed with water to remove N,N-dimethylformamide followed by drying to yield 0.53 g (84.6%, HPLC purity (method 1): 97.2%) of the title compound.

Example 2.2) TFAE as Solvent

A vessel was charged at 20° C. with 18.9 g (67.4 mmol, purity 97.5%) of N-(2-fluorophenyl)-4-[(Z)—N'-hydroxycarbamimidoyl]benzamide and 200 g (1.39 mol, purity 99%) of ethyl trifluoroacetate. 13.4 g sodium methanolate (74.4 mmol, 30% w/w in methanol) was added within 3 minutes and the reaction was stirred for 16 hours. Then, all volatiles were removed under reduced pressure, methanol (100 mL) and water (20 mL) was added and the solids were collected by filtration. The filter cake was washed with water (2×20 mL) and dried.

Dry weight of isolated title product: 20.4 g (83.4%), HPLC purity (method 1): 96.8%.

Example 2.3) TFAE as Solvent

A vessel was charged at 20° C. with 18.9 g (67.6 mmol, purity 97.8%) of N-(2-fluorophenyl)-4-[(Z)—N'-hydroxycarbamimidoyl]benzamide and 200 g (1.39 mol, purity 99%) of ethyl trifluoroacetate. 18.3 g sodium methanolate (100 mmol, 30% w/w in methanol) was added within 5 minutes and the reaction mixture was stirred for 3 hours after which an additional portion of sodium methanolate (6.1 g, 33.3 mmol) was added. Iso-propanol (200 mL) was added, the mixture heated to 70° C. and part of the volatiles was removed. The resulting mixture was cooled to ambient temperature and stirred for 16 hours before water (200 mL) was added, which caused the product to precipitate. The title product was collected by filtration. The filter cake was washed with water (2×50 mL) and dried. Dry weight of isolated title product: 20.4 g (93.4%), HPLC purity (method 1): 98.1%.

Example 2.4) TFAE as Reagent

A flask was charged with N-(2-fluorophenyl)-4-[(Z)—N'-hydroxycarbamimidoyl]benzamide (5 g, 1 equivalent), ethanol (60 mL) and ethyl trifluoroacetate (6.5 g, 2.5 equivalents) at ambient temperature under an atmosphere of nitrogen. To this reaction mass sodium ethanolate (21% w/w in ethanol, 8.3 mL, 1.4 equivalents) was added over a period of 13 minutes at ambient temperature and then the reaction mixture was stirred for 60 minutes at ambient temperature. After completion of the reaction water (100 mL) was added and the resulting mixture was stirred for 30 minutes at ambient temperature, which caused the product to precipitate. The title product was collected by filtration. The filter cake was washed with water (50 mL) and dried under vacuum, which yielded the title product as a colorless solid in 98% (HPLC purity (method 1): 99.9%).

Example 2.5) TFAE as Reagent

A flask was charged with N-(2-fluorophenyl)-4-[(Z)—N'-hydroxycarbamimidoyl]benzamide (5 g, 1 equivalent) and toluene (100 mL) at ambient temperature under an atmosphere of nitrogen before sodium ethanolate (21% in ethanol, 11.9 mL, 2.0 equivalents) was added. Ethyl trifluoroacetate (5.2 g, 2.0 equivalents) was added and the resulting mixture was stirred for 3 hours at ambient temperature. After completion of the reaction toluene was removed under reduced pressure, water (100 mL) was added and the resulting mixture was stirred for 30 minutes at ambient temperature. The solids were collected by filtration and washed with water (50 mL). Drying under vacuum yielded the title product as a colorless solid in 96.9% (HPLC purity (method 1): 99.4%).

Example 2.6) TFAE as Reagent

A flask was charged with N-(2-fluorophenyl)-4-[(Z)—N'-hydroxycarbamimidoyl]benzamide (27.5 g, 1 equivalent) and ethanol (224 g) under an atmosphere of nitrogen. Sodium ethanolate (21% w/w in ethanol, 41 g, 1.30 equivalents) is added over a period of 10 minutes at ambient temperature and the resulting mixture was heated to 51° C. After 15 minutes at 51° C. ethyl trifluoroacetate (99%, 35 g, 2.5 equivalents) was added over a period of 35 minutes and the reaction temperature was maintained at 51° C. for 5 hours. Water (400 g) was then added over a period of 2 hours. The mixture was slowly cooled to ambient temperature and then further cooled to 10° C. The solids were collected by filtration and washed with water (2×100 mL). Drying under vacuum yielded the desired product as a colorless solid in 96.5% (HPLC purity (method 1): 98.6%).

Example 2.7) TFAE as Reagent

A flask was charged with N-(2-fluorophenyl)-4-[(Z)—N'-hydroxycarbamimidoyl]benzamide (33.2 g (98.8% purity, 1 equivalent). A mixture of methanol (76.8 g) and ethyl trifluoroacetate (37.5 g, purity 100%, 2.2 equivalents) was added under an atmosphere of nitrogen. The reaction mixture was cooled to below 20° C. and sodium methanolate (30% w/w in methanol, 25.9 g, 1.20 equivalents) was added over a period of 8 minutes at a temperature below 25° C. The resulting mixture was agitated at 25° C. for 5 hours. Demineralized water (48 g) was then added at 25° C. under agitation. The suspended solids were collected by filtration. Drying under vacuum yielded the desired product as a colorless solid in 96.2% (HPLC purity (method 1): 93.4%).

Example 3) Preparation of 3-[4-(Trichloromethyl) Phenyl]-5-(Trifluoromethyl)-1,2,4-Oxadiazole 300 g (1.31 mol) 3-(p-tolyl)-5-(trifluoromethyl)-1,2,4-oxadiazole was placed in a 500 mL quartz glass round bottom flask. 427 g chlorine (6.0 mol) was passed into the reactor, heated to 125° C., and irradiated with a Heraeus TQ 150 Watt (mercury medium pressure emitter) UV-lamp over 8 hours. After completion of the reaction the reaction mass was stripped with nitrogen to remove remaining chlorine and hydrogen chloride gas. GC analysis showed 98.7ar % product. Yield: 437 g crystalline product; 99%; melting point: 75° C.-78° C.; $^1$H-NMR ($CDCl_3$): 8.1 ppm (m, 2H, 2xCH); 8.3 ppm (m, 2H, 2xCH).

Example 4) Preparation of N-(2-fluorophenyl)-4-[5-(trifluoromethyl)-1,2,4-oxadiazol-3-yl]benzamide 150 g (0.446 mol) solid 3-[4-(trichloromethyl)phenyl]-5-(trifluoromethyl)-1,2,4-oxadiazole and 3.75 g (0.023 mol) iron(III)-chloride was filled in a 0.75 L reactor equipped with an overhead stirrer, reflux condenser and off-gas scrubber. The reactor was heated to 120° C. and 7.6 g (0.422 mol) water was dosed into the reaction mixture within 3 hours and stirred for another 30 minutes. Then the reaction mixture was cooled to 25° C. and 300 g (4.156 mol)tetrahydrofuran was added and the reaction mixture cooled to 10° C. Then a solution of 56 g 2-fluoro-aniline (0.489 mol), 50 g triethylamine (0.489 mol) and 200 g tetrahydrofuran (2.771 mol) was added in about 40 minutes, whereas the temperature of the reaction mixture was kept between 10° C. and 25° C. and the lines were flushed with 100 g (1.4 mol)tetrahydrofuran. After stirring overnight, the mixture was cooled to 5° C. and 450 mL water was added. The solid was filtered off and washed twice with 100 g cold water. A solid material was obtained, which was dried (80° C., 2 kPa) to yield 130 g (0.363 mol) of the title product. HPLC analysis (method 2) showed >98 ar % product.

Example 5) Preparation of N-methyl-4-[5-(trifluoromethyl)-1,2,4-oxadiazol-3-yl]benzamide 5 g (0.015 mol) solid 3-[4-(trichloromethyl)phenyl]-5-(trifluoromethyl)-1,2,4-oxadiazole and 0.12 g (0.74 mmol) iron(III)-chloride was filled in a 0.75 L reactor equipped with an overhead stirrer, reflux condenser and off-gas scrubber. The reactor was heated to 85° C. and 0.26 g (0.014 mol) water were dosed into the reaction mixture within 1 hour and stirred for another 40 minutes. Then the temperature was cooled to 25° C. and 14.6 g (0.222 mol)tetrahydrofuran was added and the reaction mixture cooled to 0° C. Then 27 mL (5M, 0.074 mmol) of a methylamine solution in tetrahydrofuran was added and stirred overnight at room temperature. Water and ethyl acetate were added and the phases separated. The organic phase was washed with water and dried over magnesium sulfate/activated carbon. Filtration and removal of the volatiles yielded 2.9 g (HPLC analysis (method 2): 88 ar %, 0.091 mol, retention time=0.93 min, M+=271)N-methyl-4-[5-(trifluoromethyl)-1,2,4-oxadiazol-3-yl]benzamide.

Example 6) Preparation of N-methyl-4-[5-(trifluoromethyl)-1,2,4-oxadiazol-3-yl]benzenecarbothioamide 15 g (54.8 mmol)N-methyl-4-[5-(trifluoromethyl)-1,2,4-oxadiazol-3-yl]benzamide and 3.8 g (16.9 mmmol) phosphorus(V) sulfide was dissolved in 87 g toluene and heated to 112° C. for 1 hour. The reaction mixture was treated below 100° C. with 100 g water and 100 g toluene. After phase separation at 75° C. the organic phase was separated and washed with 100 g water. The volatiles were removed in vacuo (80° C., 200 to 5 mbar) to yield 15.8 g of crude product, which was suspended in 50 mL diisopropylether and heated to 60° C. for 1 hour. After cooling to room temperature, the precipitate was filtered off and washed with 20 mL diisopropylether. After drying at 80° C. and at reduced pressure, 13.5 g (44.2 mmol, HPLC analysis (method 2): 94 ar %) N-methyl-4-[5-(trifluoromethyl)-1,2,4-oxadiazol-3-yl]benzenecarbothioamide was obtained. $^1$H-NMR (δ/ppm, $CDCl_3$, 400 MHz): 3.4 ppm, s, 3H; 7.8, s, br 1H; 7.9, d, 2H; 8.1, d, 2H).

The invention claimed is:

1. A process for preparing an oxadiazole compound of formula I,

I

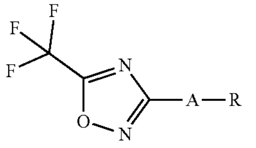

wherein

A is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein A is further unsubstituted or further substituted with additional n identical or different radicals $R^A$; wherein n is 0,1, 2, 3, or 4;

$R^A$ is independently selected from the group consisting of halogen, cyano, $C_1$-$C_6$-alkyl, $C_1$-$C_6$-haloalkyl, $C_1$-$C_6$-alkoxy, and $C_1$-$C_6$-haloalkoxy;

R is methyl, chloromethyl, hydroxymethyl, trichloromethyl, ethyl, iso-propyl, OH, SH, cyano, halogen, $CH_2F$, $CHF_2$, 2,2,2-trifluoroethyl, cyclopropyl, —C(═O)H, —C(═NOR$^2$)H, —C(═O)OH, —C(═O)OR$^1$, —C(═W)NR$^1$R$^2$, —CR$^3$R$^4$NR$^1$R$^2$, —CR$^3$R$^4$OR$^1$, —CR$^3$(═NR$^1$), —CR$^3$(═O), —CR$^3$R$^4$C(═O)OH, —CR$^3$R$^4$C(═O)R$^1$, —CR$^3$R$^4$C(═W)NR$^1$R$^2$, —OCR$^3$R$^4$C(═O)OH, —OCR$^3$R$^4$C(═O)R$^1$, —OCR$^3$R$^4$C(═W)NR$^1$R$^2$, —CR$^3$R$^4$—N(R$^2$)—C(═W)R$^1$, —CR$^3$R$^4$S(═O)$_2$R$^1$, or —CR$^3$R$^4$—N(R$^2$)—S(═O)$_2$R$^1$; wherein W is O or S;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

$R^1$ is $C_1$-$C_6$-alkyl, $C_1$-$C_6$-alkoxy, $C_3$-$C_{11}$-cycloalkyl, $C_3$-C-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —NHSO$_2$—$C_1$-$C_4$-alkyl, —C(═O)—$C_1$-$C_4$-alkyl, —C(═O)—O—$C_1$-$C_4$-alkyl, $C_1$-$C_6$-alkylsulfonyl, hydroxy$C_1$-$C_4$-alkyl, —C(═O)—NH$_2$, —C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^3$, $R^4$ independently of each other are selected from the group consisting of hydrogen, halogen, cyano, $C_1$-$C_4$-alkyl, $C_1$-$C_4$-alkenyl, $C_1$-$C_4$-alkynyl, $C_1$-$C_4$-haloalkyl and $C_1$-$C_4$-alkoxy; or $R^3$ and $R^4$ together with the carbon atom to which they are bound form a cyclopropyl group;

the process comprising reacting an amidoxime of formula II,

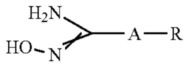

II wherein the variables A and R are as defined above for compounds of formula I, with a haloacetic ester of formula II.a,

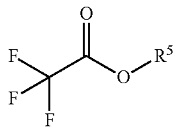

II.a wherein $R^5$ is $C_1$-$C_6$-alkyl, in the presence of a solvent and a base; whereas the base comprises a metal alkoxylate of formula IV, $[C_1\text{-}C_6\text{-alkyl-O}]_xM^{x+}$ IV wherein a metal M is an alkali metal, wherein x is 1, or M is an alkaline earth metal, wherein x is 2; and the solvent comprises an alkyl alcohol of formula III, or mixtures thereof, $C_1$-$C_6$-alkyl-OH III.

2. The process according to claim 1, wherein the metal M in the metal alkoxylate IV is sodium, potassium or magnesium.

3. The process according to claim 1, wherein the alkoxylate base of formula IV is sodium methoxide, sodium ethoxide, or a mixture thereof.

4. The process according to claim 1, wherein the solvent comprises methanol, ethanol, or a mixture thereof.

5. The process according to claim 1, wherein the solvent contains at least 1% by volume of the alkyl alcohol of formula III, or mixtures thereof, based on the total amount of solvents, whereas further solvents include auxiliary solvents, the haloacetic ester of formula II.a, or mixtures thereof.

6. The process according to claim 1, wherein the alkoxylate base of formula IV is a corresponding conjugate Bronsted base of the solvent of formula III.

7. The process according to claim 1, wherein the process is conducted at a temperature in the range of from 0° C. to 60° C.

8. The process according to claim 1, wherein the radical $R^5$ in haloacetic esters of formula II.a is methyl or ethyl.

9. The process according to claim 1, wherein an amount of the haloacetic ester of formula II.a is between 1 to 5 equivalents based on the amount of amidoxime II.

10. The process according to claim 1, wherein the amidoxime compound is of formula II.b,

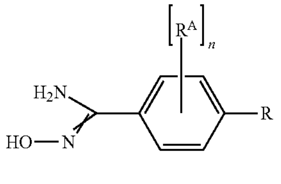

II.b wherein n is 0 or 1, and the meaning of $R^A$ and R is as defined in claim 1 for compounds of formula I, to obtain oxadiazoles of formula I.b,

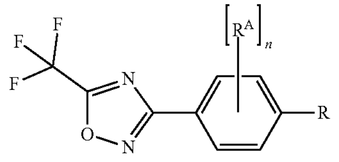

I.b wherein the variables n, $R^A$, and R have the meaning as defined for compounds II.b.

11. The process according to claim 10, wherein the variables have the following meaning:

$R^A$ is fluorine;

n is 0 or 1;

R is methyl, —C(═O)OH, —C(═O)$NR^1R^2$, —$CH_2$—N($R^2$)—C(═O)$R^1$, —$CH_2$—N($R^2$)—S(═O)$_2R^1$,

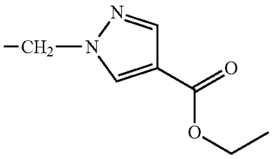

or

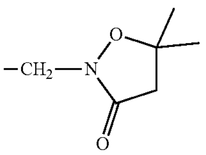

;

$R^1$ is $C_1$-$C_6$-alkly, phenyl, or cyclopropyl, wherein the phenyl ring is unsubstituted or substituted with 1, 2, 3, or 4 identical or different groups selected from halogen;

$R^2$ is hydrogen, methyl, ethyl, methoxy, ethoxy, or cyclopropyl.

12. The process according to claim 10, wherein the variables have the following meaning:

n is 0;

R is —C(═O)$NR^1R^2$;

$R^1$ is methyl, 2-methoxyiminoethyl, bicyclo[1.1.1]pentan-1-yl, 2-fluoro-phenyl, 4-fluoro-phenyl, or 2,4-difluorophenyl;

$R^2$ is hydrogen.

13. The process according to claim 12, further comprising reacting a compound of formula V.a, wherein the variables $R^1$ and $R^2$ are as defined for compound of formula II.b, to obtain the compound of formula II.b

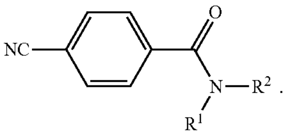

V.a

14. The process according to claim 10, wherein n is 0 and R is methyl in compounds of formula I.b and II.b, and further comprising reacting the compound of formula I.b to obtain the compound of formula I.c I.c

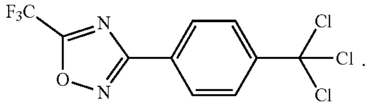

15. The process according to claim 10, wherein n is 0 and R is —C(═O)OH in compounds of formula I.b and II.b, and further comprising reacting the compound of formula I.b to obtain the compound of formula III.a III.a

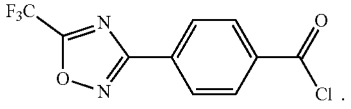

16. The process according to claim 14, further comprising the compound of formula I.c to obtain the compound of formula III.a III.a

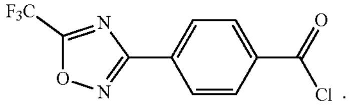

17. The process according to claim 15, further comprising reacting the compound of formula III.a with a compound of formula IV $R^1$—NH—$R^2$ IV, to obtain a compound of formula V

V

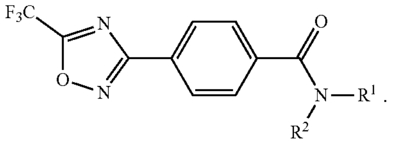

18. The process according to claim 17, further comprising reacting the compound of formula V to obtain a compound of formula VI

VI

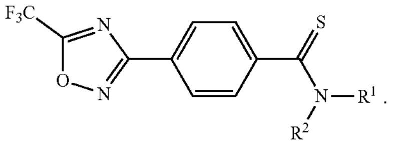

19. The process according to claim 18, wherein in compounds of formulae IV, V, and VI $R^1$ is methyl, 2-methoxyiminoethyl, bicyclo[1.1.1]pentan-1-yl, 2-fluoro-phenyl, 4-fluoro-phenyl, or 2,4-difluorophenyl; and $R^2$ is hydrogen.

* * * * *